(12) United States Patent
Schmelz et al.

(10) Patent No.: US 8,388,700 B2
(45) Date of Patent: Mar. 5, 2013

(54) COMPOSITION AND METHOD FOR COLOURING HAIR

(75) Inventors: Sandra Schmelz, Marktheidenfeld (DE); Martin Uellner, Darmstadt (DE); Fariba Ghiasi, Frankfurt (DE)

(73) Assignee: KAO Germany GmbH, Darmstadt (DE)

( * ) Notice: Subject to any disclaimer, the term of this patent is extended or adjusted under 35 U.S.C. 154(b) by 0 days.

(21) Appl. No.: 13/384,945

(22) PCT Filed: Jul. 15, 2010

(86) PCT No.: PCT/EP2010/004322
§ 371 (c)(1),
(2), (4) Date: Jan. 19, 2012

(87) PCT Pub. No.: WO2011/009561
PCT Pub. Date: Jan. 27, 2011

(65) Prior Publication Data
US 2012/0192889 A1    Aug. 2, 2012

(30) Foreign Application Priority Data
Jul. 22, 2009   (EP) .................................... 09009460

(51) Int. Cl.
*A61Q 5/10* (2006.01)

(52) U.S. Cl. ............. 8/405; 8/406; 8/435; 8/525; 8/580; 8/594; 132/202; 132/208

(58) Field of Classification Search .............. 8/405, 406, 8/435, 525, 580, 594; 132/202, 208
See application file for complete search history.

(56) References Cited

U.S. PATENT DOCUMENTS

| | | |
|---|---|---|
| 3,590,122 A | 6/1971 | Roberts et al. |
| 4,486,328 A | 12/1984 | Knott et al. |
| 5,221,286 A | 6/1993 | Singleton et al. |
| 5,431,698 A | 7/1995 | Tennigkeit et al. |
| 5,683,474 A | 11/1997 | Cotteret et al. |
| 5,785,961 A | 7/1998 | Nakama et al. |
| 5,814,106 A | 9/1998 | Audousset |
| 6,254,647 B1 | 7/2001 | Fröhling |
| 6,312,677 B1 | 11/2001 | Millequant et al. |
| 8,002,848 B2 | 8/2011 | Miyabe |
| 8,021,439 B2 | 9/2011 | Miyabe et al. |
| 2004/0133995 A1 | 7/2004 | Cottard et al. |
| 2007/0157399 A1* | 7/2007 | Nobuto et al. ................... 8/405 |
| 2007/0169286 A1 | 7/2007 | Narasimhan et al. |

FOREIGN PATENT DOCUMENTS

| | | |
|---|---|---|
| DE | 2432614 A1 | 1/1976 |
| DE | 102007048140 A1 | 4/2009 |
| EP | 524 612 A | 1/1993 |
| EP | 640 643 A | 3/1995 |
| EP | 0744175 A2 | 11/1996 |
| EP | 0925775 A2 | 6/1999 |
| EP | 0938888 A2 | 9/1999 |
| EP | 1036556 A2 | 9/2000 |
| EP | 1123693 A2 | 8/2001 |
| EP | 1219285 A2 | 7/2002 |
| EP | 1 470 812 A | 10/2004 |
| EP | 1411885 B1 | 5/2007 |
| EP | 1803436 A1 | 7/2007 |
| EP | 1982691 A1 | 10/2008 |
| EP | 2 062 562 A | 5/2009 |
| FR | 2920090 | 2/2009 |
| GB | 1083007 A | 9/1967 |
| GB | 2 188 948 A | 10/1987 |
| JP | 50 005539 | 1/1975 |
| JP | 62185008 A | 8/1987 |
| JP | 63174917 A | 7/1988 |
| JP | 5286831 | 11/1993 |
| JP | 2003206221 | 7/2003 |
| WO | 95/15144 | 6/1995 |
| WO | 01/85113 A | 11/2001 |
| WO | 02074271 A | 9/2002 |
| WO | 2005/065632 A1 | 7/2005 |
| WO | 2009047022 A1 | 4/2009 |
| WO | 2009054147 A1 | 4/2009 |
| WO | 2009054148 A1 | 4/2009 |

OTHER PUBLICATIONS

Nanho, Yukio et al., "Preparation of acidic permanent oxidative hair dyes," Chemical Abstracts, vol. 54, No. 2, Aug. 13, 1987 (abstract).
International Search Report for Related PCT/EP2010/004003, Mailed Mar. 16, 2011.
International Serach Report for Related PCT/EP2010/004004, Mailed Mar. 25, 2011.
International Search Report for Related PCT/EP2010/004005, Mailed Feb. 25, 2011.
International Search Report for Related PCT/EP2010/004006, Mailed Dec. 17, 2010.
International Search Report for Related PCT/EP2010/004007, Mailed Mar. 2, 2012.
International Search Report for Related PCT/EP2010/004321, Mailed Mar. 16, 2011.
International Search Report for Related PCT/EP2010/004322, Mailed Jan. 24, 2012.
International Search Report for Related PCT/EP2010/004323, Mailed May 3, 2012.
International Search Report for Related PCT/EP2010/004324, Mailed Jan. 24, 2012.
International Search Report for Related PCT/EP2010/004325, Mailed Oct. 29, 2010.
STIC Search Report for Related U.S. Appl. No. 13/382,788, Dated Apr. 28, 2012.

* cited by examiner

*Primary Examiner* — Eisa Elhilo
(74) *Attorney, Agent, or Firm* — Norris McLaughlin & Marcus, P.A.

(57) ABSTRACT

A composition and method oxidative colors hair based on at least one oxidative dye precursor and comprises at least one fatty acid soap, preferably selected from sodium, potassium soaps and their mixtures. The composition is preferably applied onto hair as foam from a non-aerosol foamer vessel after mixing with a composition comprising at least one oxidizing agent.

14 Claims, No Drawings

COMPOSITION AND METHOD FOR COLOURING HAIR

This application is a 371 application of PCT/EP2010/004322 filed Jul. 15, 2010, which claims foreign priority benefit under 35 U.S.C. §119 of European Application No. 09009460.8 filed Jul. 22, 2009.

Present invention relates to a composition and method for oxidative colouring hair based on at least one oxidative dye precursor and comprising at least one fatty acid soap, preferably selected from sodium, potassium soaps and their mixtures, wherein the composition is preferably applied onto hair as foam from a non-aerosol foamer vessel after mixing with a composition comprising at least one oxidizing agent Oxidative hair dyeing is a common practice and various forms have been disclosed in the literature. It is usually carried out under alkaline conditions and therefore damages hair. Due to the damage, oxidatively coloured hair is often weak does not have any strength and looses its natural volume. This is especially the case after multiple colouration and aggravated especially in case of fine hair.

On the other hand, oxidative colouring is usually carried out by mixing the alkaline composition with a composition comprising oxidizing agent in a bowl and applying the resulting composition, usually emulsion, onto hair with the aid of a brush. Although this is commonly used technique and has become a kind of tradition, it is a time consuming technique and therefore, there is a great need for new techniques which allow quick and effective application of oxidative hair dye compositions.

The present invention starts from the above problems and provides solution. First of all, the present invention provides an oxidative colouring composition which does leave hair in its natural strength and does not cause loss of volume and secondly the present invention provides a new technique for quick and effective application of the composition in a new form onto hair.

The inventor of the present invention have found out that an oxidative colouring composition comprising fatty acid soap, preferably sodium, potassium soaps and their mixtures colours hair effectively and provides hair its natural strength and elasticity and therefore, the coloured hair does not lose its volume.

Furthermore, the inventors of the present invention have found out that the oxidative colouring composition is quickly and effectively applied onto hair when it is delivered from a non-aerosol foamer vessel directly onto hair. The advantages of the technique is that the two compositions, alkaline oxidative dye comprising composition and oxidizing composition, are directly mixed in a closed vessel without contaminating hands and/or any other open vessel and the resulting mixture is directly brought onto hair as foam in a short period of time.

Thus, the first objective of the present invention is an oxidative hair dyeing composition comprising at least one oxidative dye precursor, optionally at least one coupling agent, optionally at least one direct dye and at least one fatty acid soap, preferably selected from sodium, potassium soaps and their mixtures.

The second object of the present invention is a method of colouring hair wherein two compositions A and B are mixed prior to application onto hair, wherein composition A is an acidic composition having a pH between 2 and 5 and comprising at least one oxidizing agent and composition B is an alkaline composition having a pH between 8 and 12 and comprises one or more oxidative dye precursors, optionally one or more coupling agents and optionally one or more direct dye, and wherein composition A and/or B comprises additionally one or more fatty acid soap, preferably selected from sodium, potassium soaps and their mixtures, one or more surfactants selected from anionic, non-ionic, and amphoteric ones at a concentration between 1 and 30% by weight calculated to total of compositions A or B, is applied onto hair from a vessel delivering its content in the form of a foam, preferably a squeeze foamer, processed for 1 to 45 min at a temperature in the range of 20 to 45° C. and rinsed off from hair and hair is optionally shampooed and optionally dried, preferably with a hair drier.

Further objective of the present invention is the use of the composition and the method for oxidative colouring hair.

Still further objective of the present invention is a ready to use composition for oxidative colouring hair comprising one or more oxidative dye precursors, optionally one or more coupling agents, optionally one or more direct dyes, at least one oxidizing agent, one or more fatty acid soap, preferably selected from sodium, potassium soaps and their mixtures, one or more surfactants selected from anionic, non-ionic, and amphoteric surfactants at a concentration between 1 and 30% by weight calculated to total composition, and having a pH between 5 and 12.

Still further objective of the present invention is a kit for oxidative colouring hair comprising a—a composition A which is acidic, preferably having a pH between 2 and 5 and comprising at least one oxidizing agent, b—a composition B which is an alkaline composition having a pH between 8 and 12 and comprising one or more oxidative dye precursors, optionally one or more coupling agents and optionally one or more direct dye, c—a vessel delivering its content in the form of a foam, with the condition that composition A and/or B comprises one or more fatty acid soap, preferably selected from fatty acid sodium, potassium soaps and their mixtures, and one or more surfactants selected from anionic, non-ionic, and amphoteric ones at a concentration between 1 and 30% by weight calculated to total of composition A or B.

Composition A and/or B comprises at least one fatty acid soap. In principal any fatty acid soap is suitable, however, preferred fatty acid soaps are sodium and potassium soaps. The fatty acid may be saturated or unsaturated, branched or straight and substituted or unsubstituted. Non-limiting suitable examples are soaps and especially sodium and/or potassium soaps of lauric acid, myristic acid, palmitic acid, palmitoleic acid, stearic acid, oleic acid, linoleic acid, linolenic acid, behenic acid, capric acid, caproic acid, caprylic acid, isostearic acid and ricinoleic acid as well as the ones obtained from native oils such as olive acid, corn acid, palm acid, rapeseed acid etc. Preferred are soaps of myristic acid, palmitic acid, palmitoleic acid, stearic acid, oleic acid, linoleic acid and ricinoleic acid and especially sodium and/or potassium soaps. More preferred are soaps of palmitoleic acid, oleic acid, linoleic acid and ricinoleic acid and the most preferred are soaps of oleic and linoleic acids.

Concentration of fatty acid soap varies between 0.1 and 20% preferably 0.2 and 15, more preferably 2 and 12.5 and most preferably 5 to 10% by weight calculated to the total of composition A or B.

Composition B furthermore comprises at least alkalizing agent preferably selected from ammonia (including ammonium hydroxide), carbonate and bicarbonate salts and a compound according to general formula $$R_1R_2R_3N$$

wherein $R_1$, $R_2$ and $R_3$ are same or different H, $C_1$-$C_6$ alkyl, $C_1$-$C_6$ monohydroxyalkyl or $C_2$-$C_6$ polyhydroxyalkyl with the condition that at least one of $R_1$, $R_2$ and $R_3$ is a mono or polyhydroxyalkyl.

Suitable alkanolamines according to the general formula above are monoethanolamine, diethanolamine, triethanolamine, monoethanol methylamine, monoethanoldimethylamine, di-ethanolmethylamine, monoethanolethylamine, monoethanoldiethylamine, diethanolethylamine, monoethanolpropylamine, monoethanoldipropylamine, diethanolpropylamine, monoethanolbutylamine and diethanolbutylamine.

Preferred are monoethanolamine, diethanolamine and triethanolamine. The most preferred is monoethanolamine.

Concentration of the ammonia or the amine compound according to the general formula above is depending on the alkalinity value targeted. In general it varies between 1 and 20%, preferably 1 and 15, more preferably 1 and 12.5 and most preferably 1 to 10% by weight calculated to the total of composition B.

Composition A and/or B comprises at least one surfactant selected from nonionic, anionic and amphoteric ones at a concentration between 1 and 30%, preferably 2 and 25%, more preferably 5 and 20% and most preferably 7.5 and 15% by weight calculated to total of composition A or B.

Suitable non-ionic surfactants are alkyl polyglucosides of the general formula

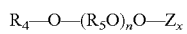

$$R_4\text{—}O\text{—}(R_5O)_n O\text{—}Z_x$$

wherein $R_4$ is an alkyl group with 8 to 18 carbon atoms, $R_5$ is an ethylene or propylene group, Z is a saccharide group with 5 to 6 carbon atoms, n is a number from 0 to 10 and x is a number between 1 and 5. Examples are decyl glucoside, carpylyl glucoside, ceteary glucoside, cocoyl ethyl glucoside, lauryl glucoside, myristyl glucoside and coco glucoside. Preferred are decyl glucoside and coco glucoside which are commercially available with the trade name Plantacare from the company Cognis.

Further non-ionic surfactants suitable are long-chain fatty acid mono- and dialkanolamides according to the general structure

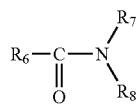

wherein $R_6$ is an alkyl chain which may be saturated or unsaturated, straight or branched, substituted or unsubstituted with a length of 8 to 22 C atoms, preferably 10 to 18 and more preferably 12 to 18 C atoms, $R_7$ and $R_8$ are same or different H, $C_1$ to $C_4$ alkyl or hydroxyl alkyl, preferably $C_2$ hydroxy alkyl with the condition that at least one of the $R_7$ and $R_8$ is not H.

Suitable non-limiting examples are behenoyl monoethanolamide, coco monoethanolamide, isostearoyl monoethanolamide, lauroyl monoethanolamide, myristoyl monoethanolamide, oleoyl monoethanolamide, ricinoleoyl monoethanolamide, stearoyl monoethanolamide, behenoyl diethanolamide, caproyl diethanolamide, cocoyl diethanolamide, isostearoyl diethanolamide, lauroyl diethanolamide, lineloyl monoethanolamide, myristoyl monoethanolamide, oleoyl monoethanolamide, palmitoyl diethanolamide, ricinoleoyl monoethanolamide and stearoyl monoethanolamide, Further additionally useful non-ionic surfactants are, for example, the various sorbitan esters, such as polyethylene glycol sorbitan stearic acid ester, fatty acid polyglycol esters or poly-condensates of ethyleneoxide and propyleneoxide, as they are on the market, for example, under the trade name "Pluronics®".

Another type of nonionic surfactants are $C_{10}$-$C_{22}$-fatty alcohol ethoxylates. Especially suited are $C_{10}$-$C_{22}$-fatty alcohol ethers with the average degree of ethoxylation between 1 and 50, preferably 5 and 50, more preferably 10 to 50. Suitable examples are oleth-2, oleth-3, oleth-4, oleth-5, oleth-6, oleth-7, oleth-8, oleth-9, oleth-10, oleth-11, oleth-12, oleth-15, oleth-16, oleth-20, oleth-25, laureth-2, laureth-3, laureth-4, laureth-5, laureth-6, laureth-7, laureth-8, laureth-9, laureth-10, laureth-11, laureth-12, laureth-13, laureth-15, laureth-16, laureth-20, laureth-25, ceteth-10, ceteth-12, ceteth-14, ceteth-15, ceteth-16, ceteth-17, ceteth-20, ceteth-25, cetoleth-10, cetoleth-12, cetoleth-14, cetoleth-15, cetoleth-16, cetoleth-17, cetoleth-20, cetoleth-25, ceteareth-10, ceteareth-12, ceteareth-14, ceteareth-15, ceteareth-16, ceteareth-18, ceteareth-20, ceteareth-22, ceteareth-25, isosteareth-10, isosteareth-12, isosteareth-15, isosteareth-20, isosteareth-22, isosteareth-25, steareth-10, steareth-11, steareth-14, steareth-15, steareth-16, steareth-20, and steareth-25. Improve here!!!!

Further suitable and preferred non-ionic surfactants are glyceryl fatty acid esters according to the general formula

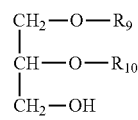

wherein $R_9$ and $R_{10}$ are same or different H, or a fatty acid group which may be saturated or unsaturated, branched or straight, substituted or unsubstituted with a C number between 10 and 22 with the condition at least one of the $R_9$ and $R_{10}$ is a fatty acyl group. The esters according the above general structure has preferably C number between 12 and 18 and more preferably 14 and 18. In particular glyceryl steric acid esters are preferred.

Most preferred glyceryl fatty acid esters are glyceryl stearate and glyceryl distearate.

Further non-ionic surfactants within the meaning of the present invention are polyalkyleneglycol ether of fatty acid glyceride or partial glyceride with at least 20 polyalkylene units, especially with 20 to 150, more preferably 20 to 100, most preferably 30 to 75 polyethyleneglycol units. Examples to those are PEG-30 hydrogenated castor oil, PEG-35 hydrogenated castor oil, PEG-40 hydrogenated castor oil, PEG-45 hydrogenated castor oil, PEG-50 hydrogenated castor oil, PEG-55 hydrogenated castor oil, PEG-60 hydrogenated castor oil, PEG-65 hydrogenated castor oil, PEG-80 hydrogenated castor oil, PEG-100 hydrogenated castor oil, PEG-200 hydrogenated castor oil, PEG-35 castor oil, PEG-50 castor oil, PEG-55 castor oil, PEG-60 castor oil, PEG-80 castor oil, PEG-100 castor oil. Additional examples of similar compounds can be found in the cosmetic ingredient dictionaries and cosmetic textbooks.

Further suitable non-ionic surfactants within the meaning of present invention are glycol fatty acid esters according to the general structure

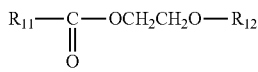

wherein $R_{11}$ is a saturated or unsaturated, branched or straight, substituted or unsubstituted alkyl with a 9 to 21 C atoms and $R_{12}$ is H or a saturated or unsaturated, branched or straight, substituted or unsubstituted acyl with 10 to 22 C atoms.

Suitable non-limiting examples are glycol cetearate, glycol dibehenate, glycol dilaurate, glycol dioleate, glycol stearate, glycol distearate, glycol oleate, glycol palmitate, glycol ricinoleate, and glycol stearate SE. Most preferred are glycol stearate SE, glycol stearate and glycol distearate.

Further suitable non-ionic surfactants are ethoxylated and/or propoxylated silicone surfactants. Non-limiting suitable examples are PEG/PPG 3/10 dimethicone, PEG/PPG 4/12 dimethicone, PEG/PPG 6/4 dimethicone, PEG/PPG 6/11dimethicone, PEG/PPG 8/14 dimethicone, PEG/PPG 8/26 dimethicone, PEG/PPG 12/16 dimethicone, PEG/PPG 12/18 dimethicone, PEG/PPG 15/15 dimethicone, PEG/PPG 17/18 dimethicone, PEG/PPG 18/12 dimethicone, PEG/PPG 18/18 dimethicone, PEG/PPG 19/19 dimethicone, PEG/PPG 15/20 dimethicone, PEG/PPG 20/20 dimethicone, PEG/PPG 20/23 dimethicone, PEG/PPG 20/29 dimethicone, PEG/PPG 22/23 dimethicone, PEG/PPG 22/24 dimethicone, PEG/PPG 25/25 dimethicone, PEG/PPG 27/27 dimethicone, PEG/PPG 20/29 dimethicone and PEG/PPG 20/29 dimethicone.

Among the non-ionic surfactants mentioned above alkyl polyglucosides and ethoxylated fatty alcohols are the most preferred ones.

Nonlimiting suitable examples of anionic surfactants are the sulfate, sulfonate, carboxylate and alkyl phosphate type, especially, of course, those customarily used $C_{10}$-$C_{18}$-alkyl sulfates, and in particular the respective ether sulfates, for example, $C_{12}$-$C_{14}$-alkyl ether sulfate, lauryl ether sulfate, especially with 1 to 4 ethylene oxide groups in the molecule, monoglyceride (ether) sulfates, fatty acid amide sulfates obtained by ethoxylation and subsequent sulfatation of fatty acid alkanolamides, and the alkali salts thereof, as well as the salts of long-chain mono- and dialkyl phosphates and their salts.

Particular reference is made to the fatty alcohol ether sulfates of the general structure

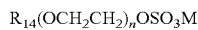

Wherein $R_{14}$ is a saturated or unsaturated, straight or branched, substituted or unsubstituted alkyl chain with 10 to 18 C atoms, n is from 1 to 5 and M is a cation, preferably ammonium, sodium or potassium.

Suitable examples are ammonium capryleth sulphate, ammonium C12-15 pareth sulphate, ammonium laureth sulphate, ammonium laureth-5 sulphate, ammonium myreth sulphate, DEA C12-13 pareth-3 sulphate, DEA laureth sulphate, DEA myreth sulphate, diethylamine laureth sulphate, magnesium coceth sulphate, magnesium laureth sulphate, magnesium laureth-5 sulphate, magnesium myreth sulphate, magnesium oleth sulphate, MEA laureth sulphate, MIPA C12-15 pareth sulphate, MIPA laureth sulphate, sodium coceth sulphate, sodium C9-15 pareth-3 sulphate, sodium C10-15 pareth-3 sulphate, sodium C12-16 pareth-2 sulphate, sodium C12-13 pareth sulphate, sodium C12-14 pareth-3 sulphate, sodium C12-15 pareth sulphate, sodium C12-15 pareth-3 sulphate, sodium C13-15 pareth-3 sulphate, sodium doceth sulphate, sodium laneth sulphate, sodium laureth sulphate, sodium laureth-5 sulphate, sodium myreth sulphate, sodium oleth sulphate, TEA laureth sulphate, TEA laneth sulphate and TIPA laureth sulphate.

Further anionic surfactants of the carboxylate type are alkyl polyether carboxylic acids and the salts thereof of the formula

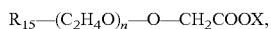

wherein $R_{15}$ is a $C_8$-$C_{20}$-alkyl group, preferably a $C_{12}$-$C_{14}$-alkyl group, n is a number from 1 to 20, preferably 2 to 17, and X is H or preferably a cation of the group sodium, potassium, magnesium and ammonium, which can optionally be hydroxyalkyl-substituted, as well as alkyl amido polyether carboxylic acids of the general formula

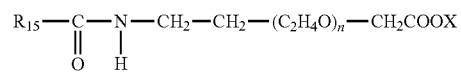

wherein $R_{15}$ and X have the above meanings, and n is in particular a number from 1 to 10, preferably 2.5 to 5.

Further suitable anionic surfactants are also $C_8$-$C_{22}$-acyl aminocarboxylic acids or the water-soluble salts thereof. Suitable ones are N-lauroyl glutamate, in particular as sodium salt, as well as, for example, N-lauroyl sarcosinate, N—$C_{12}$-$C_{18}$-acyl asparaginic acid, N-myristoyl sarcosinate, N-oleoyl sarcosinate, N-lauroyl methylalanine, N-lauroyl lysine and N-lauroyl aminopropyl glycine, preferably in form of the water-soluble alkali or ammonium, in particular the sodium salts thereof, preferably in admixture with the above-named anionic surfactants.

Among the anionic surfactants most preferred are alkyl sulfates and/or alkyl ether sulfates and among them sodium lauryl or laureth sulfates and their mixtures are most preferred.

Suitable amphoteric surfactants are in particular the various known betaines such as alkyl betaines, fatty acid amidoalkyl betaines and sulfobetaines, for example, lauryl hydroxysulfobetaine; long-chain alkyl amino acids, such as cocoaminoacetate, cocoaminopropionate and sodium cocoamphopropionate and -acetate have also proven suitable.

In detail, it is possible to use betaines of the structure

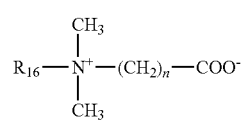

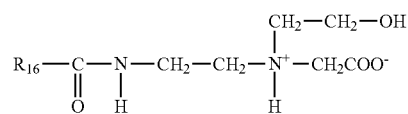

wherein $R_{16}$ is a $C_8$-$C_{18}$-alkyl group and n is 1 to 3; sulfobetaines of the structure

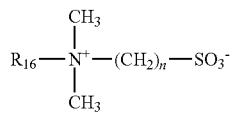

wherein $R_{16}$ and n are same as above;
and amidoalkyl betaines of the structure

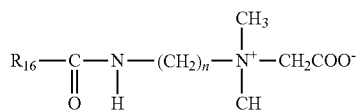

wherein $R_{16}$ and n are same as above.

Suitable nonlimiting examples are almondamidopropyl betaine, apricotamidopropyl betaine, avocadoamidopropyl betaine, babasuamidopropyl betaine, behenamidopropyl betaine, cocamidopropyl betaine, lauramidopropyl betaine, myristylamidopropyl betaine, oleamidopropyl betaine, olivamidopropyl betaine, palmamidopropyl betaine, palmitamidopropyl betaine, ricinoleamidopropyl betaine, sesamamidopropyl betaine, soyamidopropyl betaine, stearamidopropyl betaine, behenyl betaine, cetyl betaine, myristyl betaine, lauryl betaine, coco betaine, decyl betaine, oleyl betaine, stearyl betaine, tallow betaine, cocamidopropyl hydroxysultaine, coco hydroxysultaine, coco sultaine, lauramidopropyl hydroxysultaine, lauryl hydroxysultaine, myristamidopropyl hydroxysultaine, oleamidopropyl hydroxysultaine and lauryl sultaine Preferred amphoteric surfactants are of betaine types such as coco betaine and cocoylamidpropyl betaine.

In a particularly preferred form of the present invention, composition A and/or B comprises at least one non-ionic surfactant and at least one anionic surfactant preferably at a weight ratio of non-ionic surfactant to anionic surfactant in the range of 10:1 to 1:5, more preferably 7:1 to 1:2, most preferably 5:1 to 1:1 and in particular 5:1 to 2:1 and optionally at least one amphoteric surfactant.

Compositions A and/or B may further comprise one or more fatty alcohol of the general formula $R_{13}$—OH wherein $R_{13}$ is a linear or branched, saturated or unsaturated, substituted or unsubstitited alkyl chain with 12 to 22 C atoms.

Suitable fatty alcohols are myristyl alcohol, cetyl alcohol, stearyl alcohol and behenyl alcohol and their mixtures. Most preferred is the mixture of cetyl and stearyl alcohol also known as cetearyl alcohol.

The concentration of one or more fatty alcohols is in the range of 0.05 to 5%, preferably 0.1 to 3.5%, more preferably 0.1 to 2.5% and most preferably 0.1 to 2% by weight calculated to total of composition A or B.

The compositions A and/or B further comprise hair-conditioning agents. Conditioning agents are selected from oily substances, non-ionic substances, cationic amphiphilic ingredients, cationic polymers or their mixtures. Cationic amphiphilic compounds are the cationic and/or cationizable surfactants and quaternary ammonium compounds.

Suitable cationic and/or cationizable surfactants are with the general formula $R_{17}$-A-$R_{18}$—B wherein $R_{17}$ is a saturated or unsaturated, straight or branched alkyl group with 8 to 24 C atoms, $R_{18}$ is a straight or branched alkyl group with 1 to 4 C atoms, A is a group selected from O,

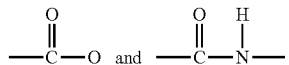

and B is selected from

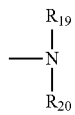

wherein $R_{19}$ and $R_{20}$ are the same or different is H or an alkyl with 1 to 4 C atoms, hydroxyl alkyl with 1 to 4 C atoms and di hydroxyl alkyl with 2 to 4 C atoms,

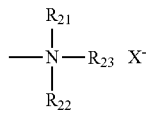

$R_{21}$, and $R_{22}$ are the same or different, an alkyl with 1 to 4 C atoms, hydroxyl alkyl with 1 to 4 C atoms and di hydroxyl alkyl with 2 to 4 C atoms, $R_{23}$ is an alkyl with 1 to 4 C atoms, hydroxyl alkyl with 1 to 4 C atoms or di hydroxyl alkyl with 2 to 4 C atoms and

—$R_{18}$-A-$R_{17}$ wherein $R_{17}$, A and $R_{18}$ have the above meaning and X is chloride, bromide, methosulfate,
or
a quaternary ammonium surfactant according to the general formula

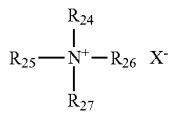

where $R2_4$ is a saturated or unsaturated, branched or non-branched alkyl chain with 8-24 C atoms and $R_{25}$ is unsaturated or saturated, branched or non-branched alkyl chain with 1-24 C atoms and $R_{26}$ and $R_{27}$ are lower alkyl chain with 1 to 4 carbon atoms which may be substituted with one or more hydroxyl groups, and X is anion such as chloride, bromide, methosulfate.

Non-limiting suitable examples are stearyloxypropyl amine, palmityloxypropyl amine, stearyloxypropyldimethyl amine, stearyloxypropyldiethyl amine, stearyloxyethyldimethyl amine, stearyloxyethyl amine, myristyloxypropyl amine, myristyloxypropyldimethyl amine, palmitamidopropyl amine, palmitamidopropyl methylamine, palmitamidopropyl diethylamine, palmitamidopropyl dibutylamine, palmitamidopropyl buylamine, palmitamidopropyl dipropylamine, palmitamidopropyl propylamine, palmitamidopropyl dihydroxyethylamine, palmitamidopropyl hydroxyethylamine, palmitamidopropyl dihydroxypropylamine, palmitamidopropyl hydroxypropylamine, lauramidopropyl amine, lauramidopropyl methylamine, lauramidopropyl diethylamine, lauramidopropyl dibutylamine, lauramidopropyl buylamine, lauramidopropyl dipropylamine, lauramidopropyl propylamine, lauramidopropyl dihydroxyethylamine, lauramidopropyl hydroxyethylamine, lauramidopropyl dihydroxypropylamine, lauramidopropyl hydroxypropylamine, stearamidopropyl amine, stearamidopropyl methylamine, stearamidopropyl diethylamine, stearamidopropyl dibutylamine, stearamidopropyl butylamine, stearamidopropyl dipropylamine, behenamidopropyl propylamine, behenamidopropyl dihydroxyethylamine, behenamidopropyl hydroxyethylamine, behenamidopropyl dihydroxypropylamine, behenamidopropyl hydroxypropylamine, behenamidopropyl amine, behenamidopropyl methylamine, behenamidopropyl diethylamine, behenamidopropyl dibutylamine, behenamidopropyl butylamine, behenamidopropyl dipropylamine, behenamidopropyl propylamine, behenamidopropyl dihydroxyethylamine, behenamidopropyl hydroxyethylamine, behenamidopropyl dihydroxypropylamine, behenamidopropyl hydroxypropylamine, dipalmitamidopropyl methylamine, dipalmitamidopropyl ethylamine, dipalmitamidopropyl butylamine, dipalmitamidopropyl propylamine, dipalmitamidopropyl hydroxyethylamine, dipalmitamidopropyl hydroxypropylamine, dilauramidopropyl amine, dilauramidopropyl methylamine, dilauramidopropyl buylamine, dilauramidopropyl hydroxyethylamine, dilauramidopropyl hydroxypropylamine, distearamidopropyl amine, distearamidopropyl methylamine, dibehenamidopropyl propylamine, dibehenamidopropyl hydroxyethylamine, palmitoamidopropyl trimethyl ammonium chloride, stearamidopropyl trimethylammonium chloride, behenamidopropyl tri hydroxyethalmonium chloride, distearylamidopropyl dimethyl ammonium chloride, dicetylamidodihydroxyethyl ammonium chloride, palmitoylpropyl amine, palmitoylpropyl methylamine, palmitoylpropyl diethylamine, palmitoylpropyl dibutylamine, palmitoylpropyl buylamine, palmitoylpropyl dipropylamine, palmitoylpropyl propylamine, palmitoylpropyl dihydroxyethylamine, palmitoylpropyl hydroxyethylamine, palmitoylpropyl dihydroxypropylamine, palmitoylpropyl hydroxypropylamine, myristoylpropyl amine, myristoylpropyl methylamine, myristoylpropyl diethylamine, myristoylpropyl dibutylamine, myristoylpropyl buylamine, myristoylpropyl dipropylamine, myristoylpropyl propylamine, myristoylpropyl dihydroxyethylamine, myristoylpropyl hydroxyethylamine, myristoylpropyl dihydroxypropylamine, myristoylpropyl hydroxypropylamine, stearoylpropyl amine, stearoylpropyl methylamine, stearoylpropyl diethylamine, stearoylpropyl dibutylamine, stearoylpropyl butylamine, stearoylpropyl dipropylamine, behenylpropyl propylamine, behenylpropyl dihydroxyethylamine, behenylpropyl hydroxyethylamine, behenylpropyl dihydroxypropylamine, behenylpropyl hydroxypropylamine, behenylpropyl amine, behenylpropyl methylamine, behenylpropyl diethylamine, behenylpropyl dibutylamine, behenylpropyl butylamine, behenylpropyl dipropylamine, behenylpropyl propylamine, behenylpropyl dihydroxyethylamine, behenylpropyl hydroxyethylamine, behenylpropyl dihydroxypropylamine, behenylpropyl hydroxypropylamine, dipalmitoylpropyl methylamine, dipalmitoylpropyl ethylamine, dipalmitylpropyl butylamine, dipalmitylpropyl propylamine, dipalmitylpropyl hydroxyethylamine, dipalmitylpropyl hydroxypropylamine, dilauroylpropyl amine, dilauroylpropyl methylamine, dilauroylpropyl buylamine, dilauroylpropyl hydroxyethylamine, dilauroylpropyl hydroxypropylamine, distearylpropyl amine, distearylpropyl methylamine, dibehenylpropyl propylamine, dibehenylpropyl hydroxyethylamine, palmitylpropyl trimethyl ammonium chloride, stearylpropyl trimethylammonium chloride, behenylpropyl tri hydroxyethalmonium chloride, distearylpropyl dimethyl ammonium chloride, dicetyldihydroxyethyl ammonium chloride, dioleoylethylhydroxyethylmonium methosulfate, dicocoylethylhydroxyethylmonium methosulfate, cetyltrimethyl ammonium chloride, steartrimonium chloride, behentrimonium chloride, myristyltrimethyl ammonium chloride, distearyldimethyl ammonium chloride, and dibehenyldimethyl ammonium chloride.

Oily substances are selected from such as silicone oils, either volatile or non-volatile, natural and synthetic oils. Among silicone oils those can be added to the compositions include dimethicone, dimethiconol, polydimethylsiloxane, DC fluid ranges from Dow Corning, as well as aminated silicones such as amodimethicone, aminopropyl phenyl trimethicone; arylated silicones with one to 5 phenyl groups in its molecule such as trimethylpentaphenyl trisiloxane, phenyl trimethicone, triphenly trimethicone and cyclic siloxanes such as cyclomethicone, cyclotrisiloxane, cyclopentasiliox-ane, cycloheptasiloxane and cyclotrisiloxane. Natural oils such as olive oil, almond oil, avocado oil, wheatgerm oil and ricinus oil may be included as conditioning agents in the composition B.

Synthetic oils may be included in composition B as conditioning agent such as mineral oil, alkyl esters of fatty acids such as isopropyl myristate, palmitate, stearate and isostearate, oleyl oleate, isocetyl stearate, hexyl laurate, dibutyl adipate, dioctyl-adipate, myristyl myristate and oleyl erucate.

Further conditioning agents may be polyols such as glycerin, glycol and derivatives, polyethyleneglycoles known with trade names Carbowax PEG from Union Carbide and Polyox WSR range from Amerchol, polyglycerin, polyethyleneglycol mono or di fatty acid esters having general formula $R_{28}CO(OCH_2CH_2)_nOH$ or $R_{28}CO(OCH_2CH_2)_nOOCR_{29}$ where $R_{28}$ and $R_{29}$ are independent from each other saturated, unsaturated or branched or non-branched alkyl chain with 7 to 21 C atoms and n is typically 2-100.

Additionally compositions A and/or B comprise one or more cationic polymers as conditioning agents. Suitable cationic polymers are those of known with their CTFA category name Polyquaternium. Typical examples of those Polyquaternium 6, Polyquaternium 7, Polyquaternium 10, Polyquaternium 11, Polyquaternium 16, Polyquaternium 28, Polyquaternium 70, Polyquaternium 67, and Polyquaternium 87.

Preferred are Polyquaternium-6, Polyquaternium-7, Polyquaternium 10, which is a cationically derivatised cellulose compound, and cationic guar gum derivatives.

The cationic polymers also include the quaternized products of graft polymers from organopolysiloxanes and polyethyl oxazolines described in EP-A 524 612 and EP-A 640 643.

Additionally, composition A and/or B comprises at least one amphoteric polymer. Non-limiting suitable and preferred examples are Polyquaterinium-22, Polyquaterinium-35, Polyquaterinium-39, Polyquaterinium-30 and Polyquaterinium-45. The more preferred are Polyquaterinium-39 and Polyquaterinium-22 and the most preferred is Poyquaternium-22.

In a particularly preferred embodiment of the present invention, composition A and/or B comprise at least one cationic polymer, at least one amphoteric polymer and at least one silicone compound as the conditioning agents.

Conditioning compounds are comprised in compositions A and/or B at a concentration of 0.01 to 5%, preferably 0.05 to 3.5% more preferably 0.1 to 2.5% by weight calculated to the total of composition A or B.

The composition A and/or B according to the invention may also comprise further conditioning substances such as protein hydrolyzates and polypeptides, e.g., keratin hydrolyzates, collagen hydrolyzates of the type "Nutrilan®" or elastin hydrolyzates, as well as also in particular plant protein hydrolyzates, optionally, cationized protein hydrolyzates, e.g., "Gluadin®".

Additional natural plant extracts can as well form part of the composition B of the present invention. Those are incorporated usually in an amount of about 0.01% to about 10%, preferably 0.05% to 7.5%, in particular 0.1% to 5% by weight, calculated as dry residue thereof to the total of composition A or B. Suitable aqueous (e.g. steam-distilled) alcoholic or hydro-alcoholic plant extracts known per se are in particular extracts from leaves, fruits, blossoms, roots, rinds or stems of aloe, pineapple, artichoke, arnica, avocado, valerian, bamboo, green tea, blue lotus flower, henbane, birch, stinging nettle, echinacea, ivy, wild angelica, gentian, ferns, pine needles, silver weed, ginseng, broom, oat, rose hip, hamamelis, hay flowers, elderberry, hop, coltsfoot, currants, chamomile, carrots, chestnuts, clover, burr root, cocoanut, cornflower, lime blossom, lily of the valley, marine algae, balm, mistletoe, passion flower, ratanhia, marigold, rosemary, horse chestnut, pink hawthorn, sage, horsetail, yarrow, primrose, nettle, thyme, walnut, wine leaves, white hawthorn, etc.

Suitable trade products are, for example, the various "Extrapone" products and "Herbasol®". Extracts and the preparation thereof are also described in "Hagers Handbuch der pharmazeutischen Praxis", $4^{th}$ Ed.

The compositions A and/or B can comprise one or more organic solvents such as ethanol, propanol, isopropanol, benzyl alcohol, benzyloxyethanol, alkylene carbonates such as ethylene carbonate and propylene carbonate, phenoxyethanol, butanol, isobutanol, cyclohexane, cyclohexanol, hexyleneglycol, ethylenecarbonate, ethyleneglycol monoethylether, ethylene glycol monobutyl ether, ethylene glycol monophenyl ether, 1-phenylethylalcohol, 2-phenylethylalcohol, propylene glycol, o-methoxyphenol. Concentration of organic solvent can be in the range of 0.1 to 25%, preferably 0.5 to 20% by weight, calculated to total of composition A or B.

Composition B of the present invention can comprise UV filters for protection of hair from environmental influences such as loss of elasticity, loss of hair colour (bleaching effect of sun light). The UV-absorbing substance is preferably selected from the following compounds: 4-Aminobenzoic acid and the esters and salts thereof, 2-phenyl benzimidazole-5-sulfonic acid and the alkali and amine salts thereof, 4-dimethyl aminobenzoic acid and the esters and salts thereof, cinnamic acid and the esters and salts thereof, 4-methoxycinnamic acid and the esters and salts thereof, salicylic acid and the esters and salts thereof, 2,4-dihydroxybenzophenone, 2,2',4,4'-tetrahydroxy-benzophenone, 2-hydroxy-4-methoxybenzophenone and its 5-sulfonic acid or the sodium salt thereof, 2,2'-dihydroxy-4,4'-dimethoxybenzophenone, 2-hydroxy-5-chlorobenzophenone, 2,2'-dihydroxy-4-methoxy-benzophenone, 2,2'-dihydroxy-4,4'-dimethoxy-5,5'-disulfobenzo-phenone or the sodium salt thereof, 2-hydroxy-4-octyloxybenzophenone, 2-hydroxy-4-methoxy-4'-methyl benzophenone, 3-benzyl-idenecampher, 3-(4'-sulfo)-benzyl-idenebornane-2-one and the salts thereof and/or 3-(4'-methylbenzylidene)-DL-campher, polysilicone-15. The preferred amount of the UV-absorber ranges from about 0.01% to 2.5%, more preferably from 0.05% to 1% by weight, calculated to the total composition.

One or more oxidative dye precursors is (are) comprised in composition B. In principal any oxidative dye precursor is suitable. Non-limiting suitable oxidative dyestuffs precursors are tetraaminopyrimidines, in particular 2,4,5,6-tetraaminopyrimidine and the lower alkyl derivatives thereof; suitable triaminohydroxypyrimidines are, for example 4-hydroxy-2,5,6-triaminopyrimidine, 2-hydroxy-4,5,6-triaminopyrimidine and 5-hydroxy-2,4,6-triaminopyrimidine; suitable mono- and diamino dihydroxypyrimidines are, for example, 2,6-dihydroxy-4,5-diaminopyrimidine, 2,4-diamino-6-hydroxy-pyrimidine or 4,6-dihydroxy-2,5-diaminopyrimidine or the water-soluble salts thereof, aminophenol derivatives such as 4-aminophenol, 4-amino-3-methylphenol, 2-chloro-4-aminophenol, 2,6-dichloro-4-aminophenol, 2,4-diaminophenol, 2,6-dibromo-4-aminophenol and/or 2-aminophenol and water-soluble salts thereof, furthermore, phenylenediamine derivatives such as 2,5-diamino-toluene, 2-n-propyl or 2-ethyl-p-phenylene-diamine, 2,6-dimethyl-p-phenylenediamine, 2-(2,5-diaminophenyl) ethanol, 1-amino -4-bis-(2'-hydroxy-ethyl)aminobenzene, 2-(2-hydroxyethyl amino)-5-aminotoluene, 4,4'-diaminodiphenylamine, 4-aminodiphenylamine, 2-amino-5-N,N-diethyl aminotoluene, 4-amino-N-ethyl-N-isopropyl aniline, 2-chloro-p-phenylenediamine, 1-β-hydroxyethyl-2,5-diamino-4-chlorobenzene, 1-β-hydroxyethyl-2,5-diamino-4-methyl benzene, 2-methoxy-p-phenylenediamine, N,N-diethyl-p-phenylenediamine, 1-amino-4-β-methoxyethyl aminobenzene, 1-dimethyl-amino-4-aminobenzene, 1-hydroxy-2,5-diamino-4-methyl benzene, 1-hydroxymethyl-2,5-diaminobenzene, 1,2-dimethyl-2,5-diaminobenzene, 1,4-diamino isopropyl benzene and/or 1-amino-4-β-hydroxypropyl aminobenzene or the water-soluble salts thereof, pyrazole derivatives such as 1-hydroxyethyl-4,5-diaminopyrazole, 3,4-diamino-5-hydroxypyrazole, 3,5-diaminopyrazole, 3,5-diamino pyrazol-1-carboxamide, 3-amino-5-hydroxypyrazole, 1-phenyl-2-methylpyrazole, 1-phenyl-3-methyl pyrazole-5-one, 3,5-dimethyl pyrazole, 3,5-dimethylpyrazole-1-methanol, 1-methyl-4,5-diaminopyrazole, 1-methylethyl-4,5-diaminopyrazole, 1-phenylmethyl-4,5-diaminopyrazole, 1-methyl-4,5-diaminopyrazole, 1-(4-methylphenyl)methyl-4,5-diaminopyrazole, 1-methyl-3-phenyl-4,5-diaminopyrazole and the water-soluble salts. The use of the above mentioned oxidative dye precursors as mixture is also customary in hair coloring area.

The total concentration of the oxidation dyestuff precursors and/or their water soluble salts if required may vary between 0.0001% and 10%, preferably 0.001% and 7.5%, in particular 0.001% to 5% by weight, calculated to the total of composition B.

The composition B may as well comprise in addition to the oxidative dye precursors at least one coupling substance, which can be selected from resorcinol, 2-methyl resorcinol, 4-chlororesorcinol, 2-amino-4-chlorophenol, 5-amino-4-methoxy-2-methylphenol, 3-amino-phenol, 1-methyl-2-hydroxy-4-aminobenzene, 3-N,N-dimethyl aminophenol, 2,6-dihydroxy-3,5-dimethoxypyridine, 5-amino-3-methylphenol, 6-amino-3-methylphenol, 3-amino-2-methylamino-6-methoxypyridine, 2-amino-3-hydroxypyridine, 2-dimethyl-amino-5-aminopyridine, 2,6-diaminopyridine, 1,3-diamino-benzene, 1-amino-3-(2'-hydroxyethylamino)benzene, 1-amino-3-[bis(2'-hydroxyethyl)amino]benzene, α-naphthol, 4,6-dichlororesorcinol, 1,3-diamino-toluene, 1-hydroxy naphthalene, 4-hydroxy-1, 2-methylenedioxy benzene, 1,5-dihydroxy naphthalene, 1,6- dihydroxy naphthalene, 1,7-dihydroxy naphthalene, 2,7-dihydroxy naphthalene, 1-hydroxy-2-methyl naphthalene, 4-hydroxy-1.2-methyldioxy benzene, 2,4-diamino-3-chlorophenol, 5-amino-2-methoxyphenol and/or 1-methoxy-2-amino-4-(2'-hydroxyethyl amino)benzene or the water-soluble salts thereof. However, this shall not exclude the addition of further developing and coupling substances. In case oxidative dye precursors are used, preferably composition B comprises additionally at least one coupling agent.

The concentration of coupling substances is customarily adjusted to the concentration of developing, oxidative dye precursor, substances.

The composition B can further comprise additionally direct dyes of neutral, cationic and anionic character. Some examples to suitable cationic dyes are Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green 1, Basic Red 2, Basic Red 12 Basic Red 22, Basic Red 51, Basic Red 76, Basic Violet 1, Basic Violet 2, Basic Violet 3, Basic Violet 10, Basic Violet 14 and Basic Yellow 57. According to the invention, suitable cationic dyestuffs are in principal those any available on the market for cosmetic hair colouring applications. For this purpose, special reference is made to the PCT application WO 95/15144 of Ciba-Geigy AG. The content of the PCT application WO 95/15144 is by reference incorporated here.

Examples to suitable direct acting anionic dyes are Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9 and Disperse Violet 1 and their alkali metal salts such as sodium, potassium.

Some examples to those suitable neutral dyes (HC dyes), so called nitro dyes, are HC Blue No.2, HC Blue No.4, HC Blue No.5, HC Blue No.6, HC Blue No.7, HC Blue No.8, HC Blue No.9, HC Blue No.10, HC Blue No.11, HC Blue No.12, HC Blue No.13, HC Brown No.1, HC Brown No.2, HC Green No.1, HC Orange No.1, HC Orange No.2, HC Orange No.3, HC Orange No.5, HC Red BN, HC Red No.1, HC Red No.3, HC Red No.7, HC Red No.8, HC Red No.9, HC Red No.10, HC Red No.11, HC Red No.13, HC Red No.54, HC Red No.14, HC Violet BS, HC Violet No.1, HC Violet No.2, HC Yellow No.2, HC Yellow No.4, HC Yellow No.5, HC Yellow No.6, HC Yellow No.7, HC Yellow No.8, HC Yellow No.9, HC Yellow No.10, HC Yellow No.11, HC Yellow No.12, HC Yellow No.13, HC Yellow No.14, HC Yellow No.15, 2-Amino-6-chloro-4-nitrophenol, picramic acid, 1,2-Diamino-4-nitrobenzol, 1,4-Diamino-2-nitrobenzol, 3-Nitro-4-aminophenol, 1-Hydroxy-2-amino-3-nitrobenzol and 2-hydroxyethylpicramic acid.

The total concentration of the direct dyes and/or their water soluble salts is between 0.0001% and 5%, preferably 0.001% and 3.5%, in particular 0.001% to 2.5% by weight, calculated to the total of composition B.

The compositions A and/or B may further comprise an organopolysiloxane wherein at least one silicon atom is linked to an alkylene group having a hetero-atom, in particular a nitrogen atom, with a poly-(N-acyl alkyleneimine) units of the formula

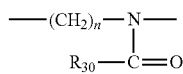

wherein n is a number from 1 to 5 and $R_{30}$ is hydrogen, a $C_1$-$C_{12}$-alkyl or cycloalkyl, aralkyl or aryl group.

Preferred organopolysiloxane polymers are those of the type disclosed in EP-A 640 643, in particular optionally quaternized aminoalkyl, in particular aminopropyl dimethyl polysiloxane/polyethyl oxazoline copolymers of the formula

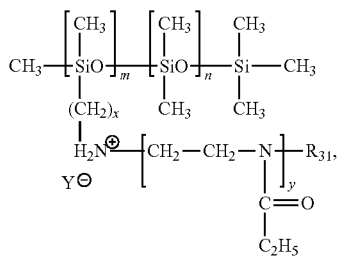

wherein m and n each are numbers from 20 to 10,000, in particular 50 to 7,000, especially 100 to 5,000, x is a number between 1 and 5, preferably 3, and y is a number from 5 to 30, $R_{31}$ is a $C_1$-$C_{12}$-alkyl or aryl group, in particular a methyl, ethyl or benzyl group, and $Y^-$ is an anion.

Especially suited are the organopolysiloxanes disclosed under the terms A-1, A-2 and A-3 on pages 12 to 13 of EP-A 640 643. The proportion of graft copolymers in the hair colouring compositions according to the invention ranges from 0.05% to 5%, preferably 0.1% to 2.5%, in particular 0.5% to 1.5% by weight, calculated to the total of composition A or B.

Another compound that may be comprised in compositions A and/or B is a ceramide type of compounds according to the general formula

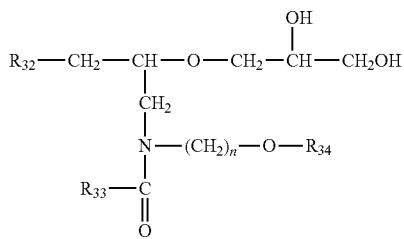

wherein $R_{32}$ and $R_{33}$ are independent from each other alkyl- or alkenyl group with 10 to 22 carbon atoms, $R_{34}$ is methyl, ethyl, n-propyl or isopropyl group and n is a number between 1 to 6, preferably 2 or 3. The concentration of the ceramide type of compound in colouring compositions of the present invention can be in the range of 0.01 to 2 and especially 0.01 to 1% by weight calculated to the total of compositions A or B.

Preferred ceramide compound is cetyl-PG-hydroxyethylpalmitamide.

Sterols, especially the phytosterols, may as well be comprised in Compositions A and/or B. Suitable ones are especially of plant origin for example ergosterol, sitosterol, stigmasterol, fucosterol, brassicasterol, fungisterol, campesterol, zymosterol, ascosterol, cerevisterol, episterol, faecosterol, spinasterol.

The concentration of ceramide may be in the range of 0.01 to 2% and phytosterol may be comprised in the range of 0.01 to 0.5% by weight calculated to the total of composition A or B.

The compositions A and/or B may further comprise one or more ubiquinone of the formula.

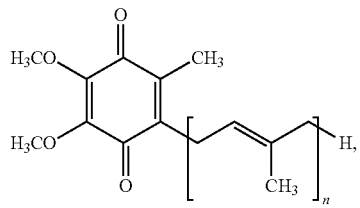

wherein n is a number from 1 to 10. The concentration of ubichinones in the compositions of the present invention can vary between 0.001% and 10% by weight, calculated to the total of composition A or B.

The composition B of the present invention may comprise compounds for accelerating (catalysts) the oxidative dyeing keratin fibres such as iodine salts i.e. potassium or sodium iodide and/or dihydroxy acetone.

Further compositions A and/or B can comprise yogurt powder at a concentration of 0.01 to 5% by weight calculated to total of the compositions A or B, which is a raw material prepared by spray drying of natural yoghurt after completion of fermentation. Yogurt powder comprises the following major components:

approximately 53.5% lactose,
approximately 25% proteins,
approximately 7.5% lactic acid,
approximately 5% minerals and trace elements,
approximately 1% vitamines, and
approximately 2% lipids.

Composition A and/or B may comprise at least one diamide compound. Preferred diamide compounds are according to the general structure

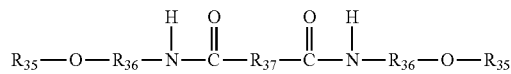

wherein $R_{35}$ is a linear or branched, saturated or unsaturated alkyl chain with 1 to 12 C atoms which may be substituted with hydroxy and/or alkoxy groups, preferably $R_{35}$ is linear or branched, saturated or unsaturated alkyl chain with 1 to 12 C atoms which may be substituted by 1 to 3 substituents selected from a hydroxy group and C1 to C6 alkoxy group, more preferably $R_{35}$ is a unsubstituted alkyl group with 1 to 12 C atoms, and alkyl group with 2 to 12 C atoms substituted by one or two hydroxyl groups, by one alkoxy group with 1 to 6 C atoms or by one hydroxyl and one alkoxy group with 2 to 6 C atoms, $R_{36}$ is linear or branched alkyl chain with 1 to 5 C atoms, preferably linear or branched alkyl chain with 2 to 5 C atoms and more preferably an alkyl chain with 2 to 3 C atoms, and $R_{37}$ linear or branched, saturated or unsaturated alkyl chain with 1 to 22 C atoms, preferably linear or branched, saturated or unsaturated alkyl chain with 11 to 22 C atoms.

Preferred individual diamide compounds are the ones according to the formula A to G.

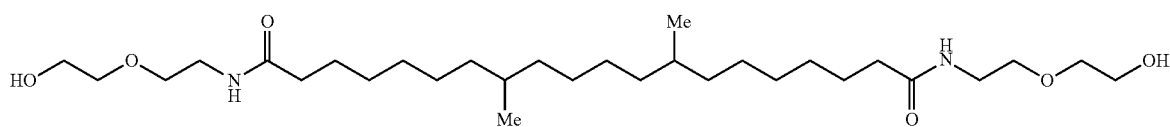

(A)

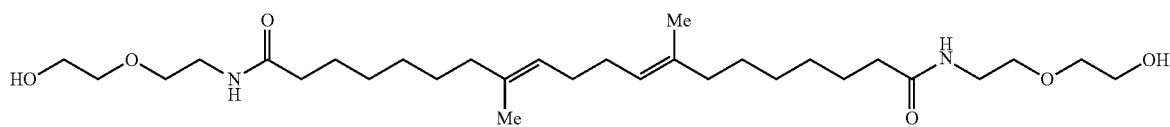

(B)

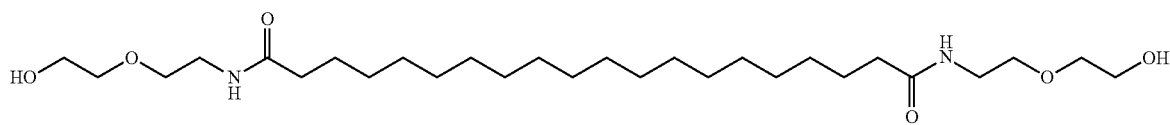

(C)

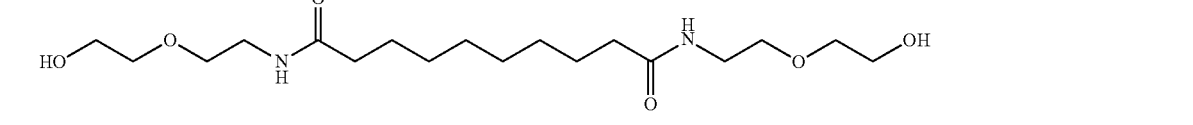

(D)

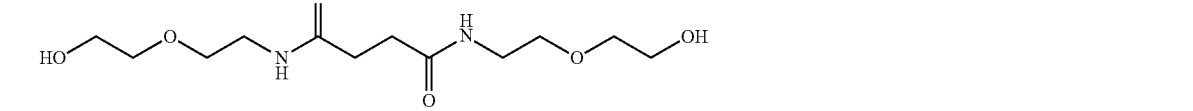

(E)

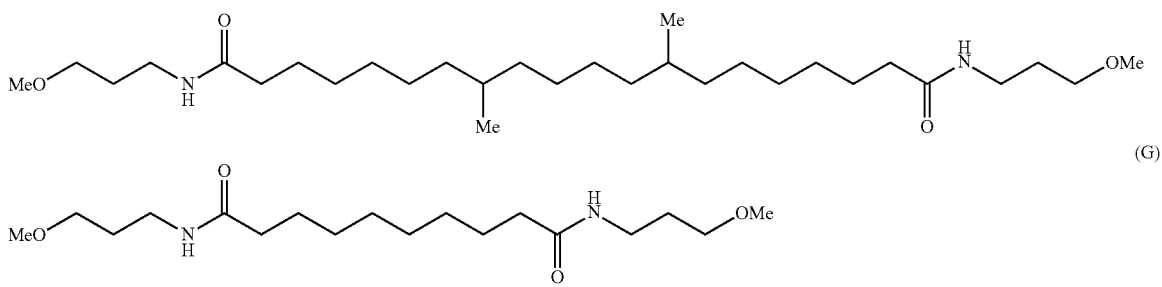

Particularly preferred diamide compound is the compound F which is bis (methoxypropylamido) isodocosane and commercially available from Kao Corporation—Japan.

Concentration of diamide compounds in the compositions A and/or B of the present invention is in the range of 0.001 to 5%, preferably 0.002 to 3% more preferably 0.005 to 2% and most preferably 0.01 to 1% by weight calculated to total of the compositions A or B.

Compositions A and/or B may further comprise particulate matter such as synthetic mica. Use of synthetic mica coated with metal oxide or oxides mainly in decorative cosmetics is disclosed in an international patent application of Sun Chemical Corporation published with a number WO 2005/065632 A1. In the document synthetic mica and coated synthetic mica with at least one metal oxide or oxides is disclosed in detail, the content of the document is included herewith by reference.

Suitable metal oxide or oxides for coating synthetic mica are titanium dioxide, chromium oxide, ferric oxide or mixtures thereof. In the present invention the preferred is synthetic mica coated with titanium dioxide. Such materials are commercially available from Sun Chemical Corporation and are known with their INCI names Synthetic Fluorphologopite.

The particle size distribution of synthetic mica coated with a metal oxide or oxides is in the range of 1 to 750 µm, preferably 1 to 250 µm, more preferably 1 to 100 µm and most preferably 20 to 95 µm. The particle sizes referred are relating to the volume particle size distribution meaning that particles found in the coated synthetic mica having volume particle size in the given ranges.

Concentration of synthetic mica coated with at least metal oxide or oxides is from 0.001 to 10%, preferably 0.05 to 7.5%, more preferably 0.1 to 5% and most preferably 0.25 to 2.5% by weight calculated to total of the compositions A or B.

Composition B may further comprise one or more dipeptide. Non-limiting examples to the suitable dipeptides are the ones commercially available and known with their INCI name as Dipeptide-1, Dipeptide-2, Dipeptide-3, Dipeptide-4, Dipeptide-5, Dipeptide-6, Dipeptide-7, Dipeptide-8, and carnosine. The most preferred is carnosine and is containing β-alanin and L-histidine.

Concentration of at least one dipeptide is in the range of 0.01 to 5%, preferably 0.05 to 3% and more preferably 0.1 to 2.5% and most preferably 0.2 to 1.5% by weight calculated to the total of the compositions A or B.

Composition A comprises at least one oxidizing agent, preferably at a concentration of at least 0.5% by weight calculated to total of composition A, preferably between 1 and 12% and more preferably 1 and 9% and most preferably 2 and 6% and in particular 2 to 3% by weight calculated to total of composition A.

In principal any oxidizing agent is suitable such as hydrogen peroxide, urea peroxide, melamine peroxide and perborate salts. The most preferred is hydrogen peroxide.

Composition A and/or B can further comprise ingredients commonly used in compositions comprising oxidizing agents such as stabilizers for peroxide compounds such as phenacetin, salicylic acid, chelating agents such as etidronic acid, EDTA and/or their salts, organic or inorganic acids such as phosphoric acid, lactic acid, for adjusting pH, surfactants in order to increase miscibility and solubilising aid for water insoluble and/or sparingly soluble substances such as fragrances and anti-foaming agents such as silicone compounds.

Compositions A and B are mixed at a weight ratio of Composition A to Composition B in the range between 5:1 and 1:5, preferably between 3:1 and 1:3, more preferably between 2:1 and 1:2, and most preferably between 2:1 and 1:1. pH of the composition thus obtained and ready to use is in the range between 5 and 12, preferably between 6 and 11, more preferably between 6.5 and 11 most preferably between 8 and 10.5.

Compositions a and/or B comprises additionally at least one inorganic salt at a concentration of 0.1 to 15%, preferably 0.1 and 10%, more preferably 0.5 to 7.5 and most preferably 1 to 5% by weight calculated to total or composition A or B.

It has been found out that the viscosity of the mixed composition plays an important factor in carrying out the process in a short period of time because the mixed composition is applied onto hair from a vessel delivering its content in the form of foam. In order to have easy and quick application and in order to secure homogeneous effect, the composition resulting from mixing the two compositions, composition A and B, has a viscosity below 1500 mPa·s., preferably below 1000 mPa·s. and more preferably 750 mPa·s. and most preferably below 500 mPa·s measured at 20° C. with a rotation viscosimeter, preferably with a Brookfiled viscosimetre with a suitable spindle and at a rotation speed. It should be noted that the compositions A and/or B may have prior to mixing different consistencies even going over the given ranges. The above given values are valid only for the mixture.

The following example is to illustrate the invention but not limit it.

EXAMPLE 1

|  | % by weight |
|---|---|
| Composition A | |
| Hydrogen peroxide | 3.0 |
| Phosphoric acid | q.s. to pH 3.0 |
| Phenacetin | 0.1 |

-continued

| | % by weight |
|---|---|
| EDTA | 0.3 |
| Water | q.s. to 100 |
| Composition B | |
| Decyl glucoside | 8.0 |
| Potassium oleate | 1.0 |
| Sodium laureth sulphate | 3.0 |
| Ethanol | 13.0 |
| Dimethicone | 0.1 |
| Polyquaternium-10 | 0.1 |
| Polyquaternium-22 | 0.1 |
| Monoethanolamine | 5.0 |
| EDTA | 0.5 |
| Sodium chloride | 5.0 |
| Sodium sulfite | 0.5 |
| p-touene diamine sulfate | 2.0 |
| Resorcinol | 0.75 |
| Fragrance | 0.5 |
| Water | q.s. to 100 |

The Composition B had a pH of 10.5

The above compositions A and B were mixed in a foamer vessel at a weight ratio of 1:1 (A:B) and the ready to use composition had a pH of 9.5 and viscosity of approximately 200 mPa·s. measured at 20° C. The mixed composition was applied onto hair in the form of foam and processed for 30 min and rinsed off from hair.

The dyed hair was easily combable and had its natural strength and elasticity and volume.

The invention claimed is:

1. A method of oxidative colouring hair wherein two compositions A and B are mixed prior to application onto hair, wherein composition A is an acidic composition having a pH between 2 and 5 and comprising at least one oxidizing agent and composition B is an alkaline composition having a pH between 8 and 12 and comprises one or more oxidative dye precursors, optionally one or more coupling agents and optionally one or more direct dye, and wherein composition A and/or B comprises additionally one or more fatty acid soap selected from sodium, potassium soaps and their mixtures, one or more surfactants selected from anionic, non-ionic, and amphoteric ones at a concentration between 1 and 30% by weight calculated to total of compositions A or B, is applied onto hair from a vessel delivering its content in the form of a foam, processed for 1 to 45 min at a temperature in the range of 20 to 45° C. and rinsed off from hair and hair is optionally shampooed and optionally dried.

2. The method according to claim 1, wherein the compositions A and B comprise one or more fatty acid soap at a concentration of 0.1 to 20% by weight, calculate to the total of composition A or B.

3. The method according to claim 1, wherein composition B comprises at least one alkalizing agent selected from ammonia, carbonate and bicarbonate salts and a compound according to general formula

R1R2R3N wherein R1, R2 and R3 are same or different H, C1-C6 alkyl, C1-C6 monohydroxyalkyl or C2-C6 polyhydroxyalkyl with the condition that at least one of R1, R2 and R3 is a mono or polyhydroxyalkyl.

4. The method according to claim 1, wherein non-ionic surfactant are selected from alkyl polyglucosides, fatty acid mono and dialkalonlamides, sorbitan esters, ethoxylated fatty alcohols, fatty acid mono and diglycerides, ethoxytaed trigylcerides, fatty acid mono and di glycol esters and silicone surfactants.

5. The method according to claim 1, wherein anionic surfactants are selected from fatty alcohol ether sulfates, alkyl poyether carboxylic acid surfactants, alkyl amido polyether carboxylic acid surfactants and acyl amionocarboxylic acid surfactants.

6. The method according to claim 1, wherein composition A and/or B comprises at least one non-ionic surfactant, and at least one anionic surfactant, at a weight ratio of non-ionic to anionic surfactants in the range of 10:1 to 1:5.

7. The method according to claim 1, wherein composition A and/or B comprises at least one fatty alcohol.

8. The method according to claim 1, wherein composition A and/or B comprises at least one hair conditioning agent.

9. The method according to claim 1, wherein composition A and/or B comprises at least one organic solvent.

10. The method according to claim 1, wherein composition A and/or B comprises at least one compound selected from diamide compounds, ceramides, ubichinones, organic solvents and UV filters.

11. The method according to claim 1, wherein composition B comprises oxidative dye precursor at a concentration of 0.0001 to 10% by weight calculated to total of Composition B.

12. The method according to claim 1, wherein composition A and/or B comprises at least one inorganic salt at a concentration of 0.1 to 15% by weight calculated to total of composition A or B.

13. The method according to claim 1, wherein composition A comprises hydrogen peroxide at a concentration of 0.5 to 12% by weight calculated to total of composition A.

14. A kit for oxidative colouring hair comprising
a—composition A that is acidic, having a pH between 2 and 5, and comprising at least one oxidizing agent,
b—composition B that is an alkaline composition, having a pH between 8 and 12, and comprising one or more oxidative dye precursors, optionally one or more coupling agents and optionally one or more direct dye, and
c—a vessel delivering its content in the form of a foam, with the condition that composition A and/or B comprises one or more fatty acid soap, selected from fatty acid sodium, potassium soaps and their mixtures, and one or more surfactants selected from anionic, non-ionic, and amphoteric surfactants at a concentration between 1 and 30% by weight calculated to total of composition A or B.

* * * * *

UNITED STATES PATENT AND TRADEMARK OFFICE
CERTIFICATE OF CORRECTION

PATENT NO.       : 8,388,700 B2                                    Page 1 of 1
APPLICATION NO.  : 13/384945
DATED            : March 5, 2013
INVENTOR(S)      : Schmelz et al.

It is certified that error appears in the above-identified patent and that said Letters Patent is hereby corrected as shown below:

In the Specification

Column 10, lines 62-63, "Poyquaternium-22" -- should read -- Polyquaterinium-22 --.

Column 12, line 32, "1,2" -- should read -- 1,3 --.

Signed and Sealed this
Twelfth Day of August, 2014

Michelle K. Lee
*Deputy Director of the United States Patent and Trademark Office*